(12) United States Patent
George, Jr. et al.

(10) Patent No.: US 6,458,542 B1
(45) Date of Patent: Oct. 1, 2002

(54) METHOD OF SCREENING FOR SUSCEPTIBILITY TO DRUG-INDUCED CARDIAC ARRHYTHMIA

(75) Inventors: Alfred L. George, Jr., Brentwood; Dan M. Roden, Nashville, both of TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/679,185

(22) Filed: Oct. 4, 2000

Related U.S. Application Data

(60) Provisional application No. 60/158,696, filed on Oct. 8, 1999.

(51) Int. Cl.[7] .................... C12Q 1/68; C12P 19/34; C07H 21/04
(52) U.S. Cl. .................... 435/6; 435/91.2; 536/23.5; 536/24.31; 536/24.33
(58) Field of Search .................... 435/6, 91.2, 810; 536/24.31, 24.33, 23.1, 23.5

(56) References Cited

U.S. PATENT DOCUMENTS 6,274,332 B1 * 8/2001 Keating et al. .............. 435/7.2

FOREIGN PATENT DOCUMENTS

WO   WO 97/23598   7/1997

OTHER PUBLICATIONS

Landegren et al. Science. !988. 241: 1077–1080.*
Splawski et al., "Genomic Structure of Three Long QT Syndrome Genes: KVLQT1, HERG, and KCNE1," Genomics, p. 86–97, (1998).
Tesson et al., "Exclusion of KCNE1 (IsK) as a Candidate Gene for Jervell and Lange–Nielsen Syndrome," Mol. Cell. Cardiol., p. 2051–1055, (1996).
PCT International Search Report for corresponding PCT application No. PCT/US00/27369.

* cited by examiner

Primary Examiner—Carla J. Myers
(74) Attorney, Agent, or Firm—Jenkins & Wilson, P.A.

(57) ABSTRACT

Isolated polynucleotide molecules, and peptides encoded by these molecules, are used in the analysis of human cardiac potassium channel minK subunit variants, as well as in screening and diagnostic applications relating to a D85N polymorphism in the KCNE1 gene encoding the human cardiac potassium channel minK subunit polypeptide. By analyzing biological samples from a subject, it is possible to type a human cardiac potassium channel minK subunit with regard to the KCNE1-D85N polymorphism, for example, in the context of screening for susceptibility to drug-induced cardiac arrhythmias.

16 Claims, 4 Drawing Sheets

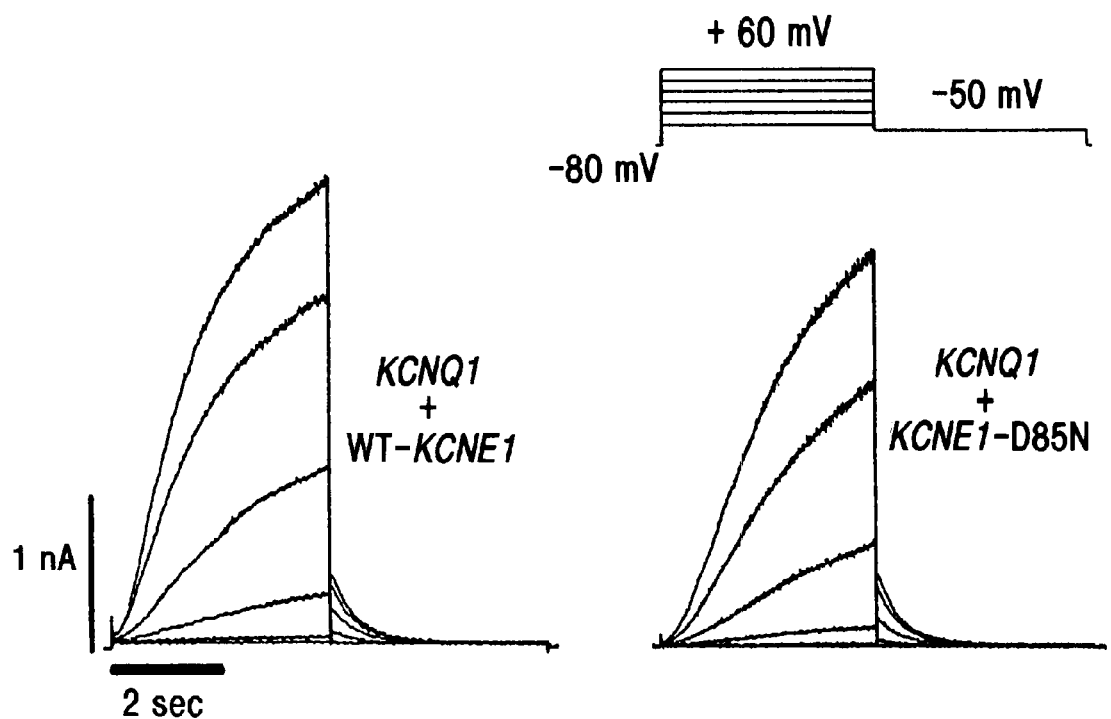
FIG. 2A  FIG. 2B
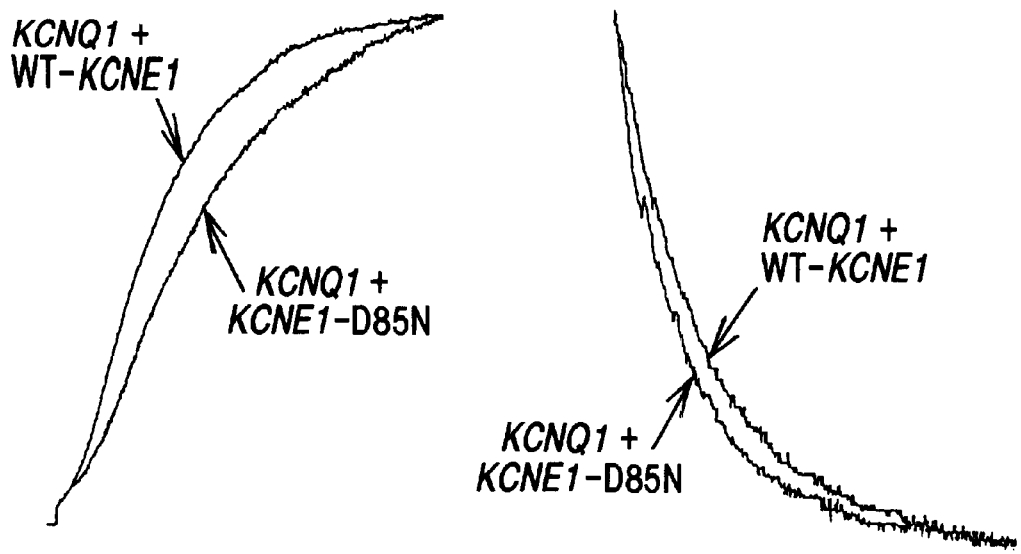
FIG. 2C  FIG. 2D

METHOD OF SCREENING FOR SUSCEPTIBILITY TO DRUG-INDUCED CARDIAC ARRHYTHMIA

CROSS REFERENCE TO RELATED APPLICATIONS

This application is based on and claims priority to U.S. Provisional Application Ser. No. 60/158,696, filed Oct. 8, 1999, the entire contents of which are herein incorporated by reference.

GRANT STATEMENT

This work was supported by NIH grant P01-HL46681. Thus, the U.S. Government has certain rights in the invention.

TECHNICAL FIELD

The present invention relates to isolated polynucleotide molecules useful for analyzing cardiac potassium channel minK subunit variants, and to screening and diagnostic uses thereof relating to a polymorphism in the KCNE1 gene encoding the cardiac potassium channel minK subunit polypeptide. Among such uses are methods for determining the susceptibility of a subject to drug-induced cardiac arrhythmias based on an analysis of a biological sample isolated from the subject.

| Table of Abbreviations | |
|---|---|
| ANOVA | analysis of variance |
| APD | action potential duration |
| Asn or N | asparagine |
| ASO | allele-specific oligonucleotide |
| Asp or D | aspartate |
| ATP | adenosine triphosphate |
| BSA | bovine serum albumin |
| CI | confidence interval |
| CL | cycle length |
| KCNE1 | gene encoding cardiac potassium channel minK subunit polypeptide |
| KCNQ1 | cardiac potassium channel gene |
| fl | full length |
| EAD | early after depolarization(s) |
| GSHosc | glutathione synthetase |
| HAT | hypoxanthine, aminopterin, thymidine |
| HERG | cardiac potassium channel gene |
| $I_{Kr}$ | rapid cardiac delayed rectifier potassium current |
| $I_{Ks}$ | slow cardiac delayed rectifier potassium current |
| KDa | kilodalton |
| KLH | keyhole limpet hemocyanin |
| L | liter(s) |
| LAT | ligation activated translation |
| LCR | ligase chain reaction |
| LQTS | long QT syndrome |
| minK | cardiac potassium channel subunit polypeptide encoded by KCNE1 |
| msec | millisecond(s) |
| NAG | n-acetyl glutamate |
| NASDA™ | nucleic acid sequence-based amplification |
| NHGRI | National Human Genome Research Institute |
| NO | nitric oxide |
| PBSCT | peripheral blood stem-cell transplantation |
| PCR | polymerase chain reaction |
| RCR | repair chain reaction |
| REF | Restriction endonuclease finger-printing |
| SCN5A | a cardiac voltage-dependent sodium channel α-subunit gene |
| sec | second |
| SSCP | single strand conformation polymorphism |
| SDA | strand displacement activation |
| WT | wild type |

BACKGROUND ART

Cardiac arrhythmias are a cause of substantial morbidity and mortality in adults. A variety of therapeutic agents commonly used to treat arrhythmias, along with other non-cardiac drugs, sometimes provoke potentially dangerous disturbances of cardiac rhythm. Prolongation of the cardiac action potential by blocking the rapidly activating cardiac delayed rectifier potassium current, $I_{Kr}$, is the desired therapeutic effect of many anti-arrhythmic agents, but is an inadvertent adverse effect of certain antihistamines, antidepressants, gastric motility promoters, and other agents. Generally without warning, 1–10% of patients receiving action potential prolonging drugs will develop marked prolongation of the electrocardiographic QT interval or polymorphic ventricular tachycardia (torsades de pointes). See Roden, D. M., *N.Engl.J.Med.* 331:785–791 (1994); Roden, D. M., *Am J Cardiol* 72:44B–49B (1993); Carlsson, L., et al., *J. Pharmacol. Exp. Ther.* 282:220–227 (1997); Mohammad, S., et al., *Am. J. Physiol. Heart Circ. Physiol.* 273:H2534–H2538(1997); Rampe, D., et al., *FEBS Lett* 417:28–32 (1997); Woosley, R. L., et al., *JAMA* 269:1532–1536 (1993); Suessbrich, H., et al., *FEBS Lett* 385:77–80 (1996); Weissenburger, J., et al., *Clin Exp Allergy* 29 (Suppl. 3):190–196 (1999); Jackman, W. M., et al., *Prog Cardiovasc Dis* 31:115–172 (1988); Lazzara, R. *Eur Heart J* 14:H88–H92(1993); Tan, H. L., et al., *Ann.Intern.Med.* 122:701–714 (1995).

Congenital long QT syndrome (LQTS) is an inherited condition of abnormal cardiac repolarization characterized clinically by an increased risk of torsades de pointes. See Keating, M. T. *Medicine (Baltimore)* 75:1–5 (1996); Vincent, G. M. *Annu. Rev. Med.* 49:263–274 (1998); Roden, D. M., et al., *Circulation* 94:1996–2012 (1996). The majority of LQTS subjects appear to harbor mutations in either of two cardiac potassium channel genes, HERG and KCNQ1 (see Curran, M. E., et al., *Cell* 80:795–803 (1995) and Wang, Q., et al., *Nature Genet* 12:17–23 (1996)), while additional cases are caused by mutations in genes encoding potassium channel regulatory subunits KCNE1 and KCNE2 (see Splawski, I., et al., *Nature Genet.* 17:338–340 (1997); Abbott, G. W., et al., *Cell* 97:175–187 (1999)), a cardiac voltage-dependent sodium channel α-subunit SCN5A (see Wang, Q., et al., *Cell* 80:805–811 (1995)), and other unidentified gene products (see Schott, J. J., et al., 57:1114–1122 (1995)).

A few anecdotal reports have attempted to associate the presence of rare sequence variants in KCNQ1 and KCNE2 to drug-induced LQT in the absence of an overt congenital phenotype. See Abbott, G. W., et al., *Cell* 97:175–187 (1999); Schulze-Bahr, E., et al., *Circulation* 96:1–211 (1997); Napolitano, C., et al., *Circulation* 96:1–211(1997); Donger, C., et al., *Circulation* 96:2778–2781 (1997); Priori, S. G., et al., *Eur Heart J* 18:324(1997). However, in these cases, the described alleles were absent in the general population, indicating that they are only rare causes of drug-induced arrhythmia susceptibility. Thus, the prevalence of drug induced cardiac arrhythmias in the general population remains unexplained and uncharacterized.

Therefore, drug-induced cardiac arrhythmias continue to represent the Achilles heel of efforts to develop safe and effective anti-arrhythmic agents. Moreover, drug induced cardiac arrhythmias also occur during treatment with non-cardiac drugs that have unintended effects on cardiac repolarization. For example, as many as 10% of patients treated with quinidine, sotalol, and ibutilide will develop excessive QT interval prolongation or exhibit the precipitous occurrence of torsade de pointes. This unpredictable adverse reaction can occur in the absence of identifiable risks factors such as hypokalemia, hypomagnesemia, concomitant treatment with other $I_{Kr}$ blockers, and recent conversion from atrial fibrillation. See Tan, H. L., et al., *Ann. Intern. Med.* 122:701–714 (1995).

A method that can predict individual susceptibility to drug-induced arrhythmias would have substantial clinical utility and would meet a long-felt need in the art. However, such a method is currently not available in the art.

DISCLOSURE OF THE INVENTION

A method of screening for susceptibility to a drug-induced cardiac arrhythmia in a subject is disclosed. The method comprises: (a) obtaining a biological sample from the subject; and (b) detecting a D85N polymorphism of a KCNE1 gene encoding a cardiac potassium channel minK subunit polypeptide in the biological sample from the subject, the presence of the D85N polymorphism indicating that the susceptibility of the subject to a drug-induced cardiac arrhythmia.

Preferably, the polymorphism of the minK polypeptide comprises a G to A transition in the single exon of the KCNE1 gene, more preferably at nucleotide 281 of a cDNA that corresponds to the KCNE1 gene. More preferably, the G to A transition at nucleotide 281 of the cDNA that corresponds to the KCNE1 gene further comprises a change in the triplet code from GAC to AAC or GAT to AAT, which encodes a KCNE1 polypeptide having an asparagine (Asn or N) moiety at amino acid 85, instead of an aspartate (Asp or D) moiety. Hence, the polymorphism is referred to as the KCNE1-D85N polymorphism.

Kits and reagents, including oligonucleotides, nucleic acid probes and antibodies suitable for use in carrying out the methods of the present invention and for use in detecting minK polypeptides and KCNE1 polynucleotides are also disclosed herein.

It is therefore an object of the present invention to provide polynucleotide molecules that can be used in analyzing a cardiac potassium channel minK subunit gene (KCNE1) in vertebrate subjects.

It is also an object of the present invention to provide for the determination of KCNE1 genotype in vertebrate subjects and particularly human subjects, based on information obtained through the analysis of nucleic acids, including genomic DNA and cDNA, derived from tissues from the subject.

It is yet another object of the present invention to provide a ready method for determining KCNE1 genotype.

It is still a further object of the present invention to provide polypeptide and polynucleotide molecules for use in generating antibodies that distinguish between the different forms of KCNE1 which constitute the KCNE1-D85N polymorphism.

It is yet a further object of the present invention to provide methods for diagnosing clinical syndromes related to and associated with the KCNE1-D85N polymorphism.

Some of the objects of the invention having been stated hereinabove, other objects will become evident as the description proceeds, when taken in connection with the accompanying Drawings and Examples as best described hereinbelow.

BRIEF DESCRIPTION OF THE DRAWINGS

FIG. 2 depicts functional characteristics of KCNQ1 co-expressed with KCNE1 alleles.

FIG. 2A depicts representative whole-cell current recordings from cells expressing KCNQ1 with WT-KCNE1. Cells were depolarized to +60 mV in 20 mV increments from a holding potential of −80 mV for 4 sec, followed by repolarization to −50 mV.

FIG. 2B depicts representative whole-cell current recordings from cells expressing KCNQ1 with KCNE1-D85N (same pulse protocol as in FIG. 2A).

FIG. 2C depicts comparison of current activation determined with a test potential of +40 mV (holding potential −80 mV) for KCNQ1+WT-KCNE1 and KCNQ1+KCNE1-D85N FIG. 2D depicts comparison of deactivating tail currents recorded at −50 mV following an activating pre-pulse to +60 mV for KCNQ1 +WT-KCNE1 and KCNQ1+KCNE1-D85N.

DETAILED DESCRIPTION OF THE INVENTION

Figure 1:
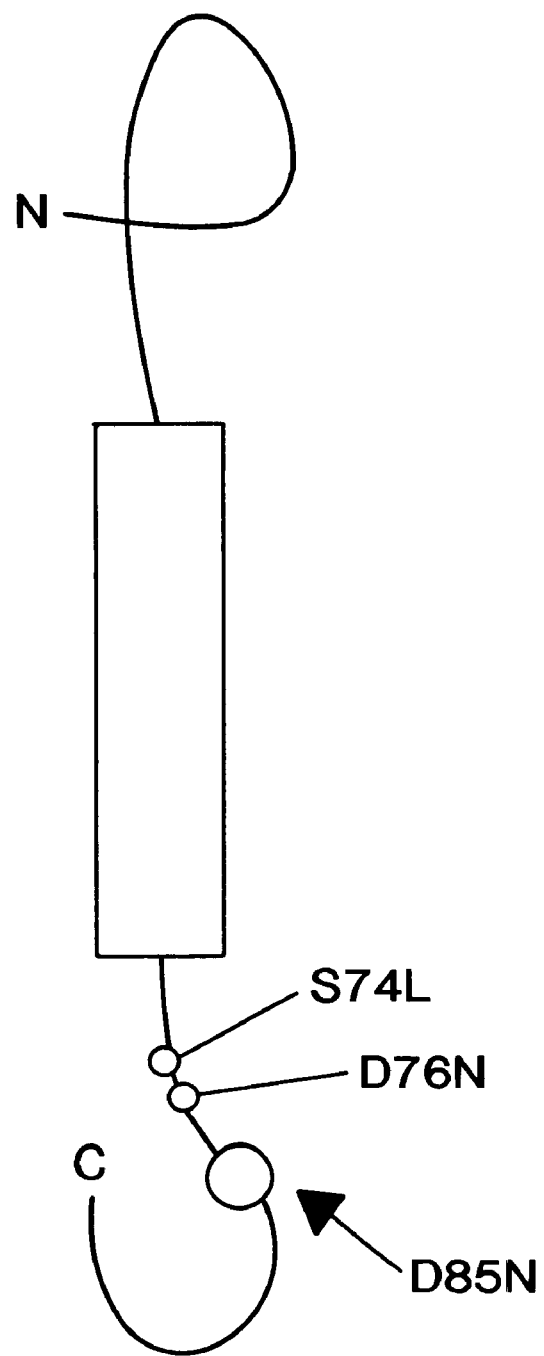
FIG. 1 is a schematic of the location of missense alleles in KCNE1. This schematic model of KCNE1 gene product illustrates two congenital LQT alleles (S74L, D76N) and the D85N polymorphism in the cytoplasmic carboxyl terminus.

Cardiac arrhythmias are a significant cause of morbidity and mortality among people living in industrialized nations. Drugs commonly used to treat this widespread problem can at times promote rather than suppress arrhythmias. Drug-induced or acquired long QT syndrome (LQTS) is a well recognized, but generally unpredictable, premonitory condition that foreshadows the occurrence of potentially fateal cardiac arrhythmias. See Roden, D. M., i N. Engl. J. Med. 331:785–791 (1994); Roden, D. M., *Am J Cardiol* 72:44B–49B (1993); Carlsson, L., et al., *J. Pharmacol. Exp. Ther.* 282:220–227 (1997); Mohammad, S., et al., *Am. J. Physiol. Heart Circ. Physiol.* 273:H2534–H2538(1997); Rampe, D., et al., *FEBS Lett* 417:28–32 (1997); Woosley, R. L., et al., *JAMA* 269:1532–1536 (1993); Suessbrich, H., et al., *FEBS Lett* 385:77–80 (1996); Weissenburger, J., et al., *Clin Exp Allergy* 29 (Suppl. 3):190–196 (1999); Jackman, W. M., et al., *Prog Cardiovasc Dis* 31:115–172 (1988); Lazzara, R. *Eur Heart J* 14:H88–H92(1993); Tan, H. L., et al., *Ann. Intern. Med.* 122:701–714 (1995).

Disclosed herein is the surprising observation that a common single nucleotide polymorphism in the KCNE1 gene encoding the potassium channel regulatory subunit minK occurs at a significantly higher frequency among patients with acquired LQT than in the general population. Also disclosed herein is the surprising observation that the polymorphism correlates to subtle kinetic changes in the minK-dependent cardiac potassium current, $I_{Ks}$, that confer an increased risk of pause-dependent, arrhythmogenic, early afterdepolarizations in the setting of partial $I_{Kr}$ block, indicating that the presence of the polymorphism confers a susceptibility to drug-induced cardiac arrhythmias.

To elaborate, the single nucleotide D85N polymorphism in the KCNE1 gene encoding the cardiac potassium channel minK subunit was more prevalent in a cohort of 98 acquired LQT subjects than in an unselected control population (7.1% vs. 1.4%, p<0.01; odds ratio 5.6, 95% Cl=1.6 to 19.2). The polymorphic allele alters the functional properties of heterologously expressed KCNQ1 cardiac potassium channels and reduces the contribution of the corresponding cardiac current, $I_{Ks}$, to cardiac repolarization. Most drugs that cause LQT block another major repolarizing cardiac potassium current, $I_{Kr}$, and computer modeling of cardiac action potentials revealed that suppression of $I_{Kr}$ in the presence of the KCNE1-D85N polymorphism produces an arrhythmogenic substrate during slow heart rates or following a long diastolic pause, two common clinical settings for the emergence of drug-induced arrhythmias. These data support the observation of reduced repolarization reserve as a risk factor for acquired LQT and provide the identity of a susceptibility allele in KCNE1.

The polymorphism is characterized by an amino acid substitution, aspartate/asparagine at amino acid 85, in the minK subunit polypeptide encoded by the KCNE1 gene. A single nucleotide change in the KCNE1 gene is responsible for the polymorphism of KCNE1. Particularly, a G to A transition with the single exon of the KCNE1 gene changes the triplet code from GAC/GAT for aspartate to AAC/AAT for asparagine and leads to the D85N amino acid change in the encoded minK subunit polypeptide. Thus, the polymorphism is referred to herein as in the claims as the "KCNE1-D85N polymorphism", "KCNE1-D85N", and/or the "D85N polymorphism".

In light of these discoveries, manipulation of nucleic acid molecules derived from the tissues of vertebrate subjects can be effected to provide for the analysis of KCNE1 genotypes, for the generation of peptides encoded by such nucleic acid molecules, and for screening and diagnostic methods relating to the KCNE1-D85N polymorphism. Nucleic acid molecules utilized in these contexts can be amplified, as described below, and generally include RNA, genomic DNA, and cDNA derived from RNA.

A. Polynucleotide Screening Methods

In accordance with the present invention, a method of screening for susceptibility to drug-induced cardiac arrhythmias in a subject is provided. The method comprising: (a) obtaining a nucleic acid sample from the subject; and (b) detecting a D85N polymorphism of a KCNE1 gene in the nucleic acid sample from the subject, the presence of the D85N polymorphism indicating that the susceptibility of the subject to drug-induced cardiac arrhythmias.

As used herein and in the claims, the term "polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus can be as small as one base pair.

As used herein and in the claims, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the KCNE1 gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

Useful nucleic acid molecules according to the present invention include those which will specifically hybridize to KCNE1 sequences in the region of the G to A transition that leads to the D85N change in the encoded minK polypeptide. Typically these are at least about 20 nucleotides in length and have the nucleotide sequence corresponding to the region of the G to A transition at base 281 of the consensus KCNE1 cDNA sequence (SEQ ID NO.:1 and GenBank accession number M26685), which changes the triplet code from GAC/GAT to AAC/AAT. The term "consensus sequence", as used herein, is meant to refer to a nucleic acid or protein sequence for KCNE1 or minK, the nucleic or amino acids of which are known to occur with high frequency in a population of individuals who carry the gene which codes for a normally functioning protein, or which nucleic acid itself has normal function.

Provided nucleic acid molecules can be labeled according to any technique known in the art, such as with radiolabels, fluorescent labels, enzymatic labels, sequence tags, etc. According to another aspect of the invention, the nucleic acid molecules contain the G to A transition at base 281 of SEQ ID NO: 1. Such molecules can be used as allele-specific oligonucleotide probes, as disclosed in the Examples presented herein.

Body samples can be tested to determine whether the KCNE1 gene contains the D85N polymorphism. Suitable body samples for testing include those comprising DNA, RNA or protein obtained from biopsies, including liver and intestinal tissue biopsies; or from blood, prenatal; or embryonic tissues, for example.

In one embodiment of the invention two pairs of isolated oligonucleotide primers are provided, e.g., SEQ ID NOS: 5 & 6 and SEQ ID NOS: 7 & 8, discussed in the Examples. These sets of primers are derived from the KCNE1 single exon, the location of the KCNE1-D85N polymorphism employed in the present invention produce 236 and 258 base pair fragments, respectively.

The oligonucleotide primers are useful in diagnosis of a subject at risk for developing drug-induced cardiac arrhythmias. The primers direct amplification of a target polynucleotide prior to sequencing. These unique KCNE1 exon oligonucleotide primers were designed and produced based upon the G to A transition associated with the KCNE1-D85N polymorphism.

In another embodiment of the invention isolated allele specific oligonucleotides (ASO) are provided, e.g., SEQ ID NO: 9. Sequences substantially similar thereto are also provided in accordance with the present invention. The allele specific oligonucleotides are useful in diagnosis of a subject at risk developing drug-induced cardiac arrhythmias. These unique KCNE1 exon oligonucleotide primers were designed and produced based upon the G to A transition associated with the KCNE1-D85N polymorphism.

The terms "substantially complementary to" or "substantially the sequence of" refer to sequences which hybridize to the sequences provided (e.g. SEQ ID NO: 9) under stringent conditions as disclosed herein and/or sequences having sufficient homology with SEQ ID NO: 9, such that the allele specific oligonucleotides of the invention hybridize to the sequence. The term "isolated" as used herein includes oligonucleotides substantially free of other nucleic acids, proteins, lipids, carbohydrates or other materials with which they can be associated, such association being either in cellular material or in a synthesis medium. A "target polynucleotide" or "target nucleic acid" refers to the nucleic acid sequence of interest e.g., a minK-encoding KCNE1 polynucleotide. Other primers which can be used for primer hybridization are readily ascertainable to those of skill in the art based upon the disclosure herein of the KCNE1-D85N polymorphism and its association with drug-induced cardiac arrhythmias The primers of the invention embrace oligonucleotides of sufficient length and appropriate sequence so as to provide initiation of polymerization on a significant number of nucleic acids in the polymorphic locus. Specifically, the term "primer" as used herein refers to a sequence comprising two or more deoxyribonucleotides or ribonucleotides, preferably more than three, and more preferably more than eight and most preferably at least about 20 nucleotides of the KCNE1 gene wherein the DNA sequence contains the G to A transition at base 281 relative to KCNE1 as set forth in SEQ ID NO:1. The allele including guanine (G) at base 281 relative to KCNE1 as set forth in SEQ ID NO: 1 is referred to herein as the "KCNE1a allele", the "D85 allele", or the "aspartate-encoding allele". The allele including adenine (A) at base 281 relative to KCNE1 as set forth in SEQ ID NO: 3 is referred to herein as the "KCNE1b allele", the "N85 allele", or the "asparagine-encoding allele".

An oligonucleotide that distinguishes between the KCNE1a and the KCNE1b alleles of the KCNE1 gene, wherein said oligonucleotide hybridizes to a portion of the KCNE1 gene that includes nucleotide 281 of a cDNA that corresponds to the KCNE1 gene when said nucleotide 281 is guanosine, but does not hybridize with said portion of said KCNE1 gene when said nucleotide 281 is adenosine is also provided in accordance with the present invention. An oligonucleotide that distinguishes between the KCNE1a and the KCNE1b alleles of the KCNE1 gene, wherein said oligonucleotide hybridizes to a portion of the KCNE1 gene that includes nucleotide 281 of the cDNA that corresponds to the KCNE1 gene when nucleotide 281 is adenosine, but does not hybridize with the portion of the KCNE1 gene when nucleotide 281 is guanosine is also provided in accordance with the present invention. Such oligonucleotides are preferably between ten and thirty bases in length. Such oligonucleotides can optionally further comprises a detectable label.

Environmental conditions conducive to synthesis include the presence of nucleoside triphosphates and an agent for polymerization, such as DNA polymerase, and a suitable temperature and pH. The primer is preferably single stranded for maximum efficiency in amplification, but can be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it can contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the transition to hybridize therewith and permit amplification of the genomic locus.

Oligonucleotide primers of the invention are employed in the amplification method which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention can be prepared using any suitable method, such as conventional phosphotriester and phosphodiester methods or automated embodiments thereof. In one such automated embodiment, diethylphosphoramidites are used as starting materials and can be synthesized as described by Beaucage et al., *Tetrahedron Letters* 22:1859–1862 (1981). One method for synthesizing oligonucleotides on a modified solid support is described in U.S. Pat. No. 4,458,066.

Any nucleic acid specimen, in purified or non-purified form, can be utilized as the starting nucleic acid or acids, providing it contains, or is suspected of containing, a nucleic acid sequence containing the polymorphic locus. Thus, the method can amplify, for example, DNA or RNA, including messenger RNA, wherein DNA or RNA can be single stranded or double stranded. In the event that RNA is to be used as a template, enzymes, and/or conditions optimal for reverse transcribing the template to DNA would be utilized. In addition, a DNA-RNA hybrid which contains one strand of each can be utilized. A mixture of nucleic acids can also be employed, or the nucleic acids produced in a previous amplification reaction herein, using the same or different primers can be so utilized. The specific nucleic acid sequence to be amplified, i.e., the polymorphic locus, can be a fraction of a larger molecule or can be present initially as a discrete molecule, so that the specific sequence constitutes the entire nucleic acid. It is not necessary that the sequence to be amplified be present initially in a pure form; it can be a minor fraction of a complex mixture, such as contained in whole human DNA.

DNA utilized herein can be extracted from a body sample, such as blood, tissue material (e.g. cardiac tissue), and the like by a variety of techniques such as that described by Maniatis et. al. in *Molecular Cloning: A Laboratory Manual*, Cold Spring Harbor, N.Y., p 280–281 (1982). If the extracted sample is impure, it can be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization can also be added together with the other reagents if it is heat stable. This synthesis (or amplification) reaction can occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization can be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described herein and this hybrid is used in subsequent steps of the method. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. *PCR. A Practical Approach*, ILR Press, Eds. McPherson et al. (1992).

The amplification products can be detected by Southern blot analysis with or without using radioactive probes. In one such method, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as dideoxy sequencing, PCR, oligomer restriction (Saiki et al., *Bio/Technology* 3:1008–1012 (1985), allele-specific oligonucleotide (ASO) probe analysis (Conner et al., *Proc. Natl. Acad. Sci. U.S.A.* 80:278 (1983), oligonucleotide ligation assays (OLAs) (Landgren et. al., *Science* 241:1007, 1988), and the like. Molecular techniques for DNA analysis have been reviewed (Landgren et. al., *Science* 242:229–237 (1988)).

Preferably, the method of amplifying is by PCR, as described herein and in U.S. Pat. Nos. 4,683,195; 4,683,202; and 4,965,188 each of which is hereby incorporated by reference; and as is commonly used by those of ordinary skill in the art. Alternative methods of amplification have been described and can also be employed as long as the KCNE1 locus amplified by PCR using primers of the invention is similarly amplified by the alternative techniques. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA.

Another nucleic acid amplification technique is nucleic acid sequence-based amplification (NASBA™) which uses reverse transcription and T7 RNA polymerase and incorporates two primers to target its cycling scheme. NASBA™ amplification can begin with either DNA or RNA and finish with either, and amplifies to about $10^8$ copies within 60 to 90 minutes.

Alternatively, nucleic acid can be amplified by ligation activated transcription (LAT). LAT works from a single-stranded template with a single primer that is partially single-stranded and partially double-stranded. Amplification is initiated by ligating a cDNA to the promoter olignucleotide and within a few hours, amplification is about $10^8$ to about $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest.

Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair.

Nucleic acid amplification by strand displacement activation (SDA) utilizes a short primer containing a recognition site for HincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the cite of the nick and begins to polymerize, displacing the initial primer strand downstream and building a new one which serves as more primer.

SDA produces greater than about a $10^7$-fold amplification in 2 hours at 37° C. Unlike PCR and LCR, SDA does not require instrumented temperature cycling. Another amplification system useful in the method of the invention is the QB Replicase System. Although PCR is the preferred method of amplification if the invention, these other methods can also be used to amplify the KCNE1 locus as described in the method of the invention. Thus, the term "amplification technique" as used herein and in the claims is meant to encompass all the foregoing methods.

In another embodiment of the invention a method is provided for diagnosing or identifying a subject having a predisposition or higher susceptibility to developing drug-induced cardiac arrhythmias, comprising sequencing a target nucleic acid of a sample from a subject by dideoxy sequencing, preferably following amplification of the target nucleic acid.

In another embodiment of the invention a method is provided for diagnosing a subject having a predisposition or higher susceptibility to developing drug-induced cardiac arrhythmias, comprising contacting a target nucleic acid of a sample from a subject with a reagent that detects the presence of the KCNE1 polymorphism and detecting the reagent.

Another method comprises contacting a target nucleic acid of a sample from a subject with a reagent that detects the presence of the G to A transition associated with the KCNE1-D85N polymorphism, and detecting the transition. A number of hybridization methods are well known to those skilled in the art. Many of them are useful in carrying out the invention.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those of ordinary skill in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. See e.g. Wetmur & Davidson, *J. Mol. Biol.* 31:349–370 (1968)).

Accordingly, a nucleotide sequence of the present invention can be used for its ability to selectively form duplex molecules with complementary stretches of the KCNE1 gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M salt at temperatures of about 50° C. to about 70° C. including particularly temperatures of about 55° C., about 60° C. and about 65° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M–0.9M salt, at temperatures ranging from about 20° C. to about 55° C., including particularly temperatures of about 25° C., about 37° C., about 45° C., and about 50° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate reagent, such as a label, for determining hybridization. A wide variety of appropriate indicator reagents are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a reagent visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, via the label.

The materials for use in the method of the invention are ideally suited for the preparation of a screening kit. Such a kit can comprise a carrier having compartments to receive in close confinement one or more containers such as vials, tubes, and the like, each of the containers comprising one of the separate elements to be used in the method. For example, one of the containers can comprise an amplifying reagent for amplifying KCNE1 DNA, such as the necessary enzyme(s) and oligonucleotide primers for amplifying target DNA from the subject.

The oligonucleotide primers include primers having a sequence selected from the group including, but not limited to: SEQ ID NOs:5–9, or primer sequences substantially complementary or substantially homologous thereto. Oligonucleotide primers comprising target flanking 5' and 3' polynucleotide sequence have substantially the sequence set forth in the flanking 5' and 3' portions of SEQ ID NOS: 1 and 3, and sequences substantially complementary or homologous thereto. Other oligonucleotide primers for amplifying KCNE1 will be readily ascertainable to those of skill in the art after review the disclosure of the present invention presented herein.

A kit in accordance with the present invention can further comprise solutions, buffers or other reagents for extracting a nucleic acid sample from a biological sample obtained from a subject. Any such reagents as would be readily apparent to one of ordinary skill in the art are within the scope of the present invention. By way of particular example, a suitable lysis buffer for the tissue or cells along with a suspension of glass beads for capturing the nucleic acid sample and an elution buffer for eluting the nucleic acid sample off of the glass beads comprise a reagent for extracting a nucleic acid sample from a biological sample obtained from a subject.

Other examples include commercially available extraction kits, such as the GENOMIC ISOLATION KIT A.S.A.P.™ (Boehringer Mannheim, Indianapolis, Ind.), Genomic DNA Isolation System (GIBCO BRL, Gaithersburg, Md.), ELU-QUIK™ DNA Purification Kit (Schleicher & Schuell, Keene, N. H.), DNA Extraction Kit (Stratagene, La Jolla, Calif.), TURBOGEN™ Isolation Kit (Invitrogen, San Diego, Calif.), and the like. Use of these kits according to the manufacturer's instructions is generally acceptable for purification of DNA prior to practicing the methods of the present invention.

G. Polypeptide/Antibody Screening Methods

In another embodiment, the present invention provides an antibody immunoreactive with a minK polypeptide or KCNE1polynucleotide. Preferably, an antibody of the invention is a monoclonal antibody. Techniques for preparing and characterizing antibodies are well known in the art (See e.g. *Antibodies A Laboratory Manual*, E. Howell and D. Lane, Cold Spring Harbor Laboratory, 1988). More preferred antibodies distinguish between the different forms of the minK polypeptide (e.g., SEQ ID NOS: 2 and 4) which comprise the KCNE1-D85N polymorphism.

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide can vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Reagents for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies, inter alia, upon the nature of the immunogen as well as the animal used for immunization. A variety of routes can be used to administer the immunogen, e.g. subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

Thus, in one aspect, the present invention contemplates a method of producing an antibody immunoreactive with a minK polypeptide encoded by a KCNE1 gene, the method comprising: (a) transfecting recombinant host cells with a KCNE1 polynucleotide that encodes the minK polypeptide; (b) culturing the host cells under conditions sufficient for expression of the polypeptide; (c) recovering the polypeptide; and (d) preparing antibodies to the polypeptide. The present invention also provides antibodies prepared according to the method described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a minK polypeptide or KCNE1 polynucleotide) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 µg of an antigen comprising a minK polypeptide. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/minK polypeptide. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/minK polypeptide. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific minK polypeptides and KCNE1 polynucleotides can be recognized as antigens, and thus identified. Once identified, those polypeptides and polynucleotides can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

The present invention thus also provides a method of screening a biological sample for the presence of a minK polypeptide encoded by a KCNE1 polynucleotide. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide. Hepatic tissues comprise particularly contemplated tissues.

Preferably, antibodies which distinguish between the D85 minK polypeptide and the N85 minK polypeptide are provided. Such antibodies can comprise polyclonal antibodies but are preferably monoclonal antibodies prepared as described hereinabove.

In accordance with a screening assay method, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary inter alia with the biological conditions used, the concentration of antibody and polypeptide and the nature of the sample (e.g., fluid or tissue sample). Techniques for determining exposure time are well known to one of ordinary skill in the art. Typically, where the sample is fluid and the concentration of polypeptide in that sample is about $10^{-1}$M, exposure time is from about 10 minutes to about 200 minutes.

The presence of polypeptide in the sample is detected by detecting the formation and presence of antibody-polypeptide conjugates. Techniques for detecting such antibody-antigen (e.g., minK subunit polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Techniques for affixing indicators to antibodies are well known in the art. Commercial kits are available.

In another aspect, the present invention provides a method of screening a biological sample for the presence of antibodies immunoreactive with a minK polypeptide encoded by a KCNE1 polynicleotide. In accordance with such a method, a biological sample is exposed to a KCNE1 polypeptide under biological conditions and for a period of time sufficient for antibody-polypeptide conjugate formation and the formed conjugates are detected.

In another aspect, the present invention contemplates screening assay kits for detecting the presence of a minK polypeptide encoded by a KCNE1 polynucleotide in biological samples, where the kits comprise a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

In another aspect, the present invention contemplates screening assay kits for detecting the presence, in a biological sample, of antibodies immunoreactive with a minK polypeptide encoded by a KCNE1 polynucleotide, the kits comprising a first container containing a minK polypeptide that immunoreacts with the antibodies, with the polypeptide present in an amount sufficient to perform at least one assay. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

Summarily, the detection and screening assays disclosed herein are used as a part of a screening method. Human KCNE1-encoding polynucleotides as well as their protein products can be readily used in clinical setting to screen for and to diagnose susceptibility to drug-induced cardiac arrhythmias in humans.

EXAMPLES

The following Examples have been included to illustrate preferred modes of the invention. Certain aspects of the following Examples are described in terms of techniques or procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only in that numerous changes, modification, and alterations can be employed without departing from the spirit and scope of the invention.

Methods and Materials Used in Examples
Study Subjects

Genomic DNA samples were obtained from 98 patients who experienced excessive prolongation of the QT interval (>600 msec) or who developed torsades de pointes during treatment with antiarrhythmic agents or various other drugs associated with acquired LQTs. Patients in this category exhibited a normal rate-corrected QT interval (QTc<450 msec) in the drug-free state. Informed consent was obtained from each study subject. Genomic DNA was isolated from peripheral blood leukocytes using standard methods. See Sambrook, J., et al., *Molecular Cloning: a Laboratory Manual* (Cold Spring Harbor, New York, N.Y., 1989).

Approximately one third of patients exhibited this phenotype remarkably early in the course of treatment, and in some cases after only the first few doses. The female:male ratio in this study population is 2.1, and 97% of patients were Caucasian. The 450 sample NHGRI Polymorphism Discovery Resource panel (Collins, F. S., et al., *Genome Research* 8:1229–1231 (1998)) was used as a control group.
Molecular Genetics Two overlapping regions of the KCNE1 coding sequence were screened for the presence of nucleotide sequence polymorphisms by single-strand conformation analysis as described by Orita, M., et al., *Proc Natl Acad Sci USA* 86:2766–2770 (1989). Oligonucleotide primer pairs used to amplify the KCNE1 coding sequence were: section I (corresponding to nucleotides 2–238 of SEQ ID NO: 1-GenBank sequence accession number M26685), forward primer: 5'-TGC AGC AGT GGA ACC TTA AT-3' (SEQ ID NO:5), reverse primer: 5'-CTT CTT GGA GCG GAT GTA GC-3' (SEQ ID NO:6); and section II (corresponding to nucleotides 178–436 of SEQ ID NO:1), forward primer: 5'-ACT GGG ATT CTT CGG CTT CT-3' (SEQ ID NO:7); reverse primer: 5'-TTT AGC CAG TGG TGG GGT TC-3' (SEQ ID NO:8). Amplification reactions were carried out using 200 ng genomic DNA, 0.5 μM primers, 0.2 mM deoxynucleotide triphosphates, and Taq polymerase.

Single-strand conformation analysis was performed on 0.5×MDE™ acrylamide based gels (FMC Corporation, Philadelphia, Pa.) electrophoresed overnight at 4 watts and stained with silver nitrate. Abnormal conformers were excised from dried gels, eluted into sterile water, reamplified using the original primers, and sequenced using dye terminator chemistry. The presence of the KCNE1-D85N polymorphism was confirmed independently on PCR amplified genomic DNA using an allele-specific oligonucleotide (ASO) hybridization assay with a $^{32}$P end labeled primer: 5'-GAG TCC AAT GCC TGG CAA-3' (SEQ ID NO:9).
Site-directed Mutagenesis Mutagenesis of human KCNE1 cDNA (SEQ ID NO:1) (encoding the minK polypeptide) using a one-step recombinant polymerase chain reaction (PCR) strategy was performed to create the D85N mutation. A forward (sense) primer, 5'-TAC ATC CGC TCC AAG AAG CTG GAG CAC TCG AAC GAC CCA TTC AAC GTC TAC ATC GAG TCC AAT GCA TGG CAA GAG AAG GAC AAG-3' (SEQ ID NO:10) spanning nt. 217–300 of SEQ ID NO:1, and a reverse primer 5'-TCG ATC GTC TAG AGA TCA GCG GCC GCT CTT-3' (SEQ ID NO:11), were used to create the mutation (changed codon underlined) and incorporate restriction sites for BstXI and XbaI in the final 266 bp product. Amplifications (20 cycles) were performed using 20 ng of KCNE1 cDNA as template and Taq DNA polymerase. Final products were purified by spin-column chromatography (kit available from Qiagen, Valencia, Calif.), digested with BstXI and XbaI, and the resulting 241 bp fragment ligated into the corresponding sites in the plasmid pRc/CMV-KCNE1. The amplified region was sequenced entirely in the final construct to verify the mutation and to exclude polymerase errors.
Cell Preparation and Transfection Chinese hamster ovary K1 (CHO-K1) cells were obtained from the American Type Culture Collection, Manassas, Va., accession no. CCL-61 and cultured in Ham's F-12 media (Gibco-BRL, Grand Island, N.Y.) supplemented with 10% fetal bovine serum, 2 mM L-glutamine, and 1% penicillin/streptomycin in an humidified, 5% $CO_2$ incubator at 37° C. Mammalian expression plasmids encoding either full-length KCNQ1 or HERG were provided by Michael Sanguinetti (University of Utah, Provo, Utah). CHO-K1 cells were transiently transfected using the Lipofectamine transfection reagent according to the supplier's instructions (Life Technologies, Inc., Rockville, Md.). Potassium channel encoding DNAs were co-transfected with a plasmid containing the CD8 antigen (provided by Dr. Richard Horn, Jefferson Medical College, Philadelphia, Pa.) to facilitate recognition of transfected cells using micro-beads conjugated to CD8 antibodies (DynaBeads™ from Dynal, Oslo, Norway) prior to electrophysiological recording. Cells were used in experiments 48 to 72 hours after transfection.

Electrophysiology and Data Analysis

Potassium currents were recorded at room temperature (20–22° C.) using the whole-cell patch clamp technique. Electrode resistances ranged from 1–2 MΩ when filled with a solution containing (in mM): 110 KCl; 5 $K_2$ATP; 2 $MgCl_2$; 10 Hepes; and 5 $K_4$BAPTA, pH 7.2. The bath solution for all experiments contained (in mM): 145 NaCl; 4 KCl; 1.8 $CaCl_2$; 1.0 $MgCl_2$; 10 Hepes; and 10 glucose, pH 7.35. Voltage-clamp command pulses were generated using pCLAMP6™ software (v6.0.4, Axon Instruments, Inc., Foster City, Calif.). Currents were filtered at 5 kHz (−3 dB, 4-pole Bessel filter). An AXOPATCH™ 200 integrating patch clamp amplifier (Axon Instruments, Inc., Foster City, Calif.) was used with series resistance compensation. Voltage-clamp protocols were employed to record $K^+$ currents over a range of membrane potentials. The holding potential for all pulse protocols was −80 mV, and specific protocols are described in the figure legends. Data were analyzed using SIGMAPLOT™ software (Jandel Scientific, San Rafael, Calif.).

The voltage-dependence of channel activation was derived by fitting tail current amplitudes (normalized to the maximum) with a Boltzmann equation:

$$I = 1/[1+\exp((-k)*(V_t - V_{1/2}))] \quad [1]$$

where $V_{1/2}$ is the membrane potential at which 50% activation occurs and k is a slope factor. For a quantitative description of deactivation, tail currents could be well fit by a monoexponential function ($y = A*e^{-(t-t_0)/\tau}$), where $t_0$ is the time at the beginning of the repolarizing voltage step, and $\tau$ is a time constant. Activation was similarly described by fitting a biexponential function to the data ($y = A_1*e^{-(t-t0)/\tau 1} + A_2*e^{-(t-t0)/\tau 2}$ where $A_1$ and $A_2$ are amplitude terms, and $\tau_1$ and $\tau_2$ are time constants). Pooled data are presented as means ± standard errors, and statistical comparisons are made by one-way or multifactorial ANOVA with p<0.05 considered significant.

Simulation of Cardiac Action Potentials

Simulations were conducted using the theoretical dynamic model of a mammalian ventricular action potential (LRd model) as described by Viswanathan, P. C., et al., *Circulation* 99:2466–2474 (1999). The model includes membrane ionic channel currents formulated mathematically using the Hodgkin-Huxley approach, as well as ionic pumps and exchangers. It also includes processes that regulate intracellular concentration changes of $Na^+$, $K^+$ and $Ca^{2+}$. For the Examples, the formulation of the slow delayed rectifier potassium current, $I_{Ks}$, was modified to fit the experimental voltage clamp data obtained from KCNQ1+ WT-KCNE1 and KCNQ1+KCNE1-D85N channels. Action potential simulations were performed by stimulation of a hypothetical cell 40 times at a constant cycle length (CL) of 1000 msec. After 40 stimuli, an additional stimulus was applied following a pause of 2500 msec.

Example 1

KCNE1 Polymorphism in Acquired LQT Patients

Because of its role in assembly of the ion channel complex underlying the slowly activating repolarizing cardiac potassium current, $I_{Ks}$, KCNE1 was examined for single strand conformational polymorphisms in patients with acquired LQTs. KCNE1 comprises a single coding exon that was successfully amplified in two overlapping segments from genomic DNA. A previously reported sequence variant (Lai, L.-P., et al., *Gene* 151:339–340 (1994)) that results in the substitution of a glycine residue for serine-38 was observed in acquired LQT patients at the same frequence as the general population suggesting that this allele was not a susceptibility factor.

A second KCNE1 polymorphism, reported by Tesson, F., et al., *J Mol Cell Cardiol* 28:2051–2055 (1996) was also observed in this population. This allele results in the replacement of Asp-85 with Asn (designated as KCNE1-D85N), a residue located in the cytoplasmic carboxyl-terminal domain of KCNE1 near two known mutations that cause congenital LQTs (FIG. 1). This polymorphism was observed in 7 of 98 (7.1%) acquired LQTs patients, and in only 1.4% of control samples from the NHGRI Polymorphism Discovery Resource panel (Yates-corrected chi-square=9.04, p=0.003). These data indicate that KCNE1-D85N is associated with increased risk of drug-induced arrhythmia (relative risk 3.1, 95% CI=1.47 to 4.76; odds ratio 5.57, 95% CI=1.64 to 19.22). All drug-induced LQTs subjects carrying KCNE1-D85N were heterozygous for this allele, and 6 of the 7 allele positive subjects were female.

Example 2

Functional Consequences of KCNE1-D85N

To determine the effects of KCNE1-D85N on cardiac potassium channel function, CHO-K1 cells were cotransfected with a recombinant KCNQ1 plasmid (encoding KvLQT1) in combination with wild-type KCNE1(WT-KCNE1) or KCNE1-D85N cDNA. Channel function was assessed with whole-cell patch clamp recording using voltage-clamp protocols optimized to examine detailed kinetic properties of the expressed potassium currents. Coexpression of KCNQ1 with either WT-KCNE1 or KCNE1-D85N produced similar slow activating outward currents that closely resemble cardiac $I_{Ks}$. The magnitudes of the expressed current (normalized to cell capacitance) measured at the end of a 4 second test pulse over a range of membrane potentials from a holding potential of −80 mV were not significantly different between groups of cells transfected with WT-KCNE1 or KCNE1-D85N (FIGS. 2A and 2B).

Next, whether KCNE1-D85N altered the gating properties of KCNQ1 was examined. The voltage-dependence of activation was not significantly different between cells transfected with WT-KCNE1 or KCNE1-D85N (WT-KCNE1: $V_{1/2}=13.4\pm4.1$ mV, k=12.6±1.1 mV, n=8; KCNE1-D85N: $V_{1/2}=20.6\pm2.7$ mV, k=14.9±1.6 mV, n=17). However, KCNE1-D85N produced slower KCNQ1 channel activation, and accelerated the rate of KCNQ1 deactivation (FIGS. 2C and 2D) as compared with WT-KCNE1. Time constants for activation determined at a test potential of +40 mV were significantly greater for KCNQ1 expressed with KCNE1-D85N than with WT-KCNE1 (KCNE1-D85N: $\tau_1=368\pm51$ msec, $\tau_2=2153\pm207$, n=16; vs WT-KCNE1: $\tau_1=220\pm30$ msec, $\tau_2=1429\pm122$, n=11; p<0.05 for both sets of values), indicating a slower time course of channel activation. Deactivation of KCNQ1, assessed by measuring the exponential decay of "tail" currents during a repolarizing voltage-step (−50 mV) following channel activation at +60 mV, was more rapid when KCNQ was co-expressed with KCNE1-D85N than when KCNQ was co-expressed with WT-KCNE1 (KCNE1-D85N: τ=295±36 msec, n=17, vs WT-KCNE1: τ=469±56 msec, n=14; p<0.05). Together the combined effects of slower activation and more rapid deactivation observed for KCNQ1 channels assembled with KCNE1-D85N (FIG. 2) suggest that $I_{Ks}$ current generated from this molecular substrate contributes less to the steady-state level of repolarizing potassium current than channel complexes containing WT-KCNE1.

Figure 3:
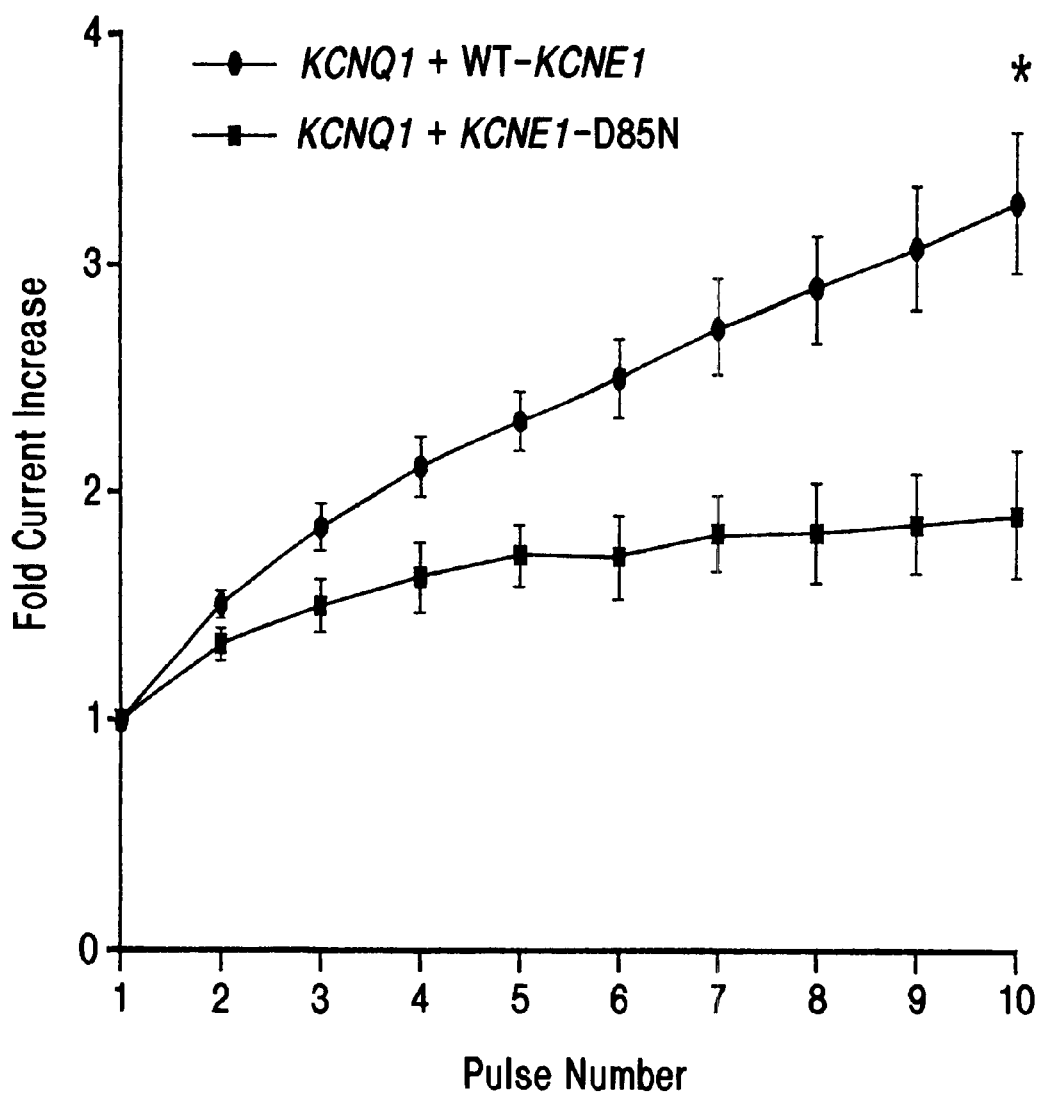
FIG. 3 is a graph depicting the effect of repetitive depolarization on function of KCNQ1 co-expressed with KCNE1 alleles. Cells expressing KCNQ1 with either WT-KCNE1 or KCNE1-D85N were repeatedly depolarized to +60 mV for 1 sec and repolarized to −50 mV for 780 msec. Data plotted are the ratios of current recorded at the end of each depolarizing pulse to that of the first depolarizing pulse. (*=p<0.05).

Because $I_{Ks}$ is a slowly activating and deactivating current that modulates the duration of the action potential primarily during repetitive stimulation, a pulse train protocol was utilized to examine the effect of KCNE1-D85N in this context. Cells expressing KCNQ1 with either WT-KCNE1 or KCNE1-D85N were repeatedly depolarized to +60 mV for 1 sec and repolarized to −50 mV for 780 msec. After 10 successive depolarizations, outward current in cells expressing WT-KCNE1 containing channel complexes had markedly increased, while only a minimal increase of current was observed in KCNE1-D85N expressing cells (FIG. 3). After the 10th pulse, WT-KCNE1 channel current increased 3.3±0.3 fold, while KCNE1-D85N current increased only 1.9±0.3 fold (p=0.015). This result illustrates the significant impact of KCNE1-D85N on the magnitude of $I_{Ks}$ during repetitive stimulation.

KCNE1 has also been demonstrated to augment expression levels of recombinant HERG channels or cellular $I_{Kr}$ in vitro (Yang, T., et al., *Circ Res* 77:1246–1253 (1995); Mcdonald, T. V., et al., *Nature* 388:289–292 (1997); Bianchi, L., et al., *Hum Mol Genet* 8:1499–1507 (1999)), but might not be its true subunit partner in vivo (Abbott, G. W., et al., *Cell* 97:175–187 (1999)). Therefore, the functional characteristics of HERG co-expressed with either WT-KCNE1 or KCNE1-D85N were compared. Current-voltage relationships, voltage-dependence of activation, and the rate of HERG inactivation were not significantly different between channel complexes formed with the two KCNE1 alleles. Sensitivity to block by 1 μM quinidine was also tested, and no difference between the two channel complexes was observed. Therefore, the impact of the KCNE1-D85N polymorphism on the function of HERG channels formed in vitro is minimal.

Example 3

Simulation of Action Potential Effects of KCNE1-D85N

The impact of the biophysical changes observed for KCNE1-D85N containing channels on cardiac repolarization cannot easily be assessed directly in the human heart. Therefore, computer simulations of cardiac action potentials that incorporated the observed kinetic changes in $I_{Ks}$ gating associated with KCNE1-D85N were utilized.

Figure 4A:
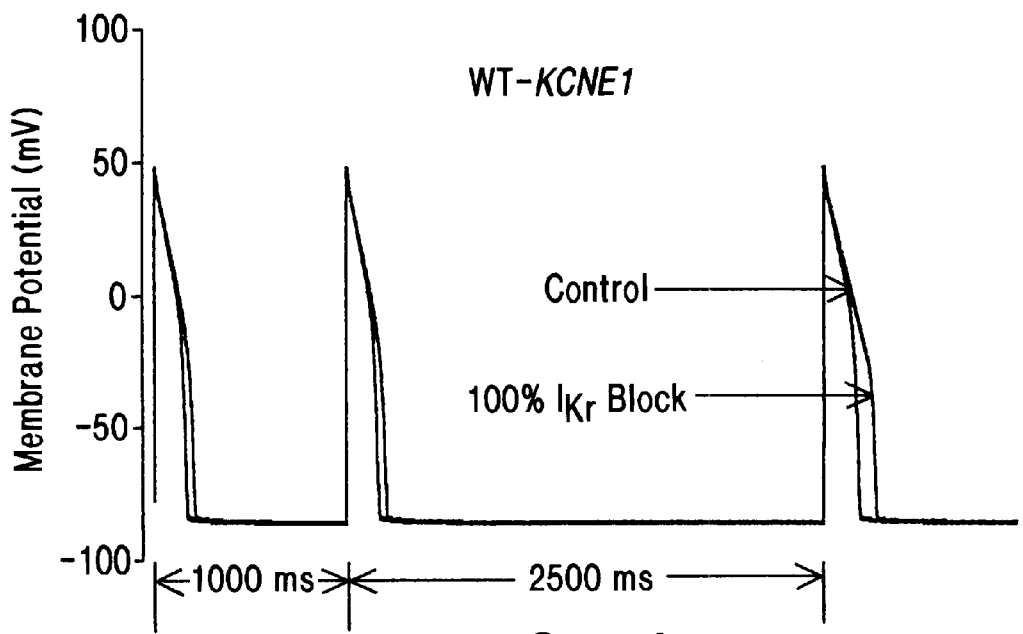
FIG. 4 depicts the simulated effects of $I_{Kr}$ block on ventricular action potentials. Results from LRd model simulations using a train of 40 action potentials (APs) followed by a brief pause (2500 msec). The last two APs are shown for two conditions: (Panel A) Data simulated with the $I_{Ks}$ characteristics of KCNQ1+WT-KCNE1. (Panel B) Data simulated with the $I_{Ks}$ characteristics of KCNQ1+KCNE1-D85N. 47% $I_{Kr}$ block was sufficient to cause EADs in KCNQ1+KCNE1-D85N (Panel B) while 100% $I_{Kr}$ block failed to produce EADs in KCNQ1+WT-KCNE1 (Panel A). For the simulations, the mathematical formulation for $I_{Ks}$ was modified from the LRd (Viswanathan, P.C., et al., *Circulation* 99:2466–2474 (1999)) to match the experimental data presented in FIG. 2 as follows: $\tau_{xs1}$=A/((7.19E−5* (v+30)/(1−EXP(−0.148*(v+30)))+B*(v+30)/(EXP(0.0687* (v+30))−1)). For KCNQ1+WT-KCNE1: A=1.2; B=0.85E− 4; $\tau_{xs2}$=6.08*$\tau_{xs1}$. For KCNQ1+KCNE1-D85N: A=1.9; B=2.1E−4; $t_{xs2}$=5.79*$t_{xs1}$.
Figure 4B:
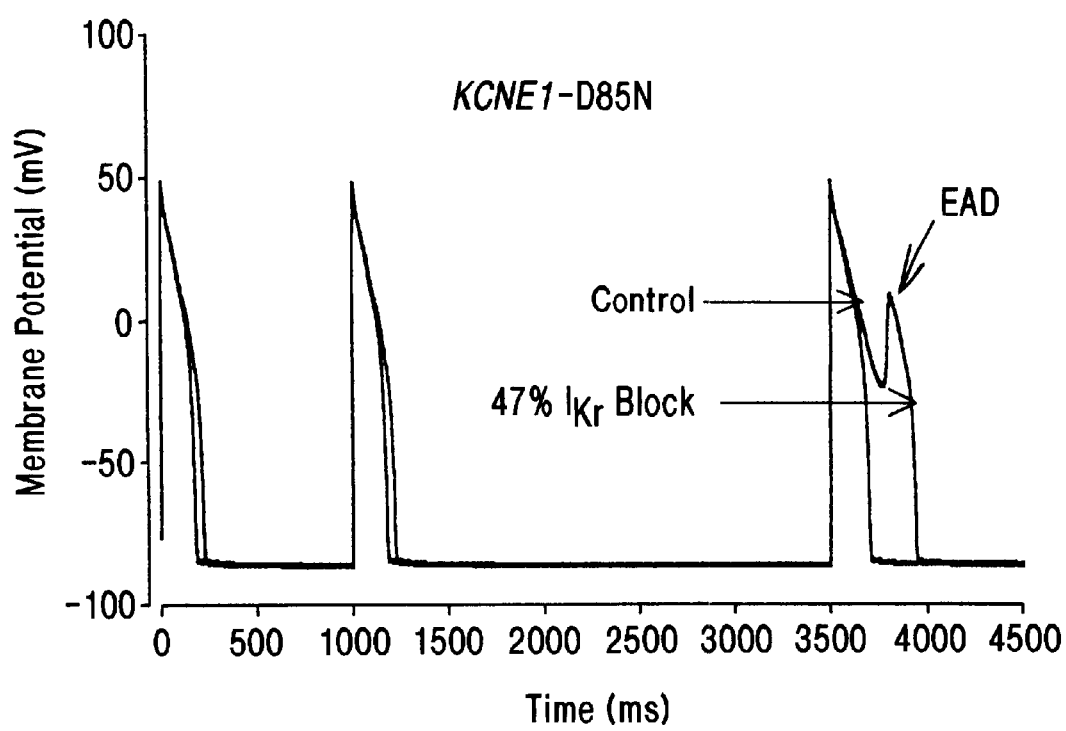

To simulate action potential changes arising from KCNE1-D85N, the mathematical formulation for wild type $I_{Ks}$ (Viswanathan, P. C., et al., *Circulation* 99:2466–2474 (1999)) was modified (see legend to FIG. 4) to reproduce the experimentally determined activation and deactivation kinetics of KCNQ1 channels expressed with either WT-KCNE1 or KCNE1-D85N (FIG. 2). This $I_{Ks}$ formulation prolonged the action potential duration ($APD_{90}$) by 18% during pacing at a constant 1000 msec cycle length due to the slower activation of KCNE1-D85N-containing channels and the resultant smaller repolarizing current. After 40 such stimuli (CL=1000 msec), insertion of a 2500 msec pause did not elicit arrhythmogenic early afterdepolarizations (EADs), consistent with the nascent KCNE1-D85N clinical phenotype. Moreover, complete $I_{Kr}$ block prolongs the $APD_{90}$ of the post-pause AP in WT-KCNE1 simulations, but this does not result in EADs (FIG. 4A). By contrast, 47% $I_{Kr}$ block is sufficient to cause EAD development in KCNE1-D85N simulations (FIG. 4B). Most of the simulation studies were conducted assuming that 100% of the channels contained KCNE1-D85N. Simulations performed with a 1:1 WT-KCNE1:KCNE1-D85N mixture demonstrated a similar propensity for EAD development that required a greater degree of $I_{Kr}$ block (83%).

Discussion of Examples

The Examples involved first identifying a cohort of patients who exhibited exaggerated QT prolongation or drug-induced torsade de pointes while being treated with anti-arrhythmic drugs and other agents known to block $I_{Kr}$, and then examining candidate genes mapped previously as congenital LQTs loci. The Examples indicate that KCNE1-D85N occurs at a significantly higher rate among drug-induced arrhythmia patients than in the general population, which further indicates that this is a candidate susceptibility allele. In this context, susceptibility is distinct from overt disease in that environmental stimuli (ie. drug treatment) or concomitant acquired disease is necessary for expression of the latent genetic defect.

The frequency of KCNE1-D85N in the general population (1.4%) indicates that this is a common polymorphism that is expected to occur in approximately 3.5 million Americans. If 1–2% of the general population is indeed at greater risk for drug-induced arrhythmias, prospective testing for KCNE1-D85N in accordance with the present invention has great utility in predicting at-risk individuals prior to initiation of anti-arrhythmic and other therapy. Once identified, such individuals are subjected to different treatment options (e.g., different medications).

The mechanism by which KCNE1-D85N confers increased risk of drug-induced arrhythmia involves the reduction in steady-state $I_{Ks}$. The Examples suggest that impairment of a physiological reserve in myocardial repolarization that normally protects individuals from the severe effects of metabolic and pharmacologic $I_{Kr}$ suppression confers susceptibility to drug-induced arrhythmia in any condition associated with reduced $I_{Kr}$. The small reduction in $I_{Ks}$ effectiveness caused by the association of KCNE1-D85N with KCNQ1 is sufficient to render myocardium more vulnerable to the occurrence of early afterdepolarizations (EADs). Based on the computer simulation of cardiac action potentials described herein, this susceptibility allele has its greatest impact during episodes of bradycardia or following a long pause during concomitant partial $I_{Kr}$ block. These simulations mimic the clinically observed pause-dependent triggering of torsade de pointes in the acquired long QT syndrome as described by El-Sherif, N., et al., *J Am Coll Cardiol* 33:1415–1423 (1999); Gilmour, R. F. J., et al., *J Am Coil Cardiol* 30:209–217 (1997).

In summary, the presence of a susceptibility polymorphism, KCNE1-D85N, in a significant proportion of patients with drug-induced arrhythmias has been demonstrated. The biophysical and electrophysiological mechanism by which this susceptibility allele confers an increased risk of arrhythmogenic substrates in the setting of pharmacologic suppression of repolarizing cardiac potassium currents has also been demonstrated.

REFERENCES

The references listed below as well as all references cited in the specification are incorporated herein by reference to the extent that they supplement, explain, provide a background for or teach methodology, techniques and/or compositions employed herein.

Abbott, G. W., et al., *Cell* 97:175–187 (1999).
Adelman et al., *DNA* 2:183 (1983).
Bachmann et al., *New England Journal of Medicine* 304:543 (1981).
Barhanin, J., et al., *Nature* 384:78–80 (1996).
Beaucage et al., *Tetrahedron Letters* 22:1859–1862 (1981).
Becker et al., *Archives of Biochemistry & Biophysics* 223:381–392 (1983).
Bianchi, L., et al., *Hum Mol Genet* 8:1499–1507 (1999).
Busjahn, A., et al., *Circulation* 99:3161–3164 (1999).
Carlsson, L., et al., *J. Pharmacol. Exp. Ther.* 282:220–227 (1997).
Choy, A. M., et al., *J Am Coll Cardiol* 34:396–401 (1999).
Clancy, C. E. & Rudy, Y., *Nature* 400:566–569 (1999).
Collins, F. S., et al., *Genome Research* 8:1229–1231 (1998).
Crea et al., *Proc. Natl. Acad. Sci. USA* 75:5765 (1978).
Curran, M. E., et al., *Cell* 80:795–803 (1995).
Donger, C., et al., *Circulation* 96:2778–2781 (1997).
Eichenlaub et al., *J. Bacteriol.* 138:559–566 (1979).
El-Sherif, N., et al., *J Am Coll Cardiol* 33:1415–1423 (1999).
Gilmour, R. F. J., et al., *J Am Coll Cardiol* 30:209–217 (1997).
Gribskov et al., *Nucl. Acids. Res.* 14:6745 (1986).
Howell et al., *Antibodies A Laboratory Manual* Cold Spring Harbor Laboratory, (1988).
Jackman, W. M., et al., *Prog Cardiovasc Dis* 31:115–172 (1988).
Jurman, M. E., et al., *Bio Techniques* 17:876–881 (1994).
Keating, M. T. *Medicine (Baltimore)* 75:1–5 (1996).
Kyte & Doolittle, *J. Mol. Biol.* 157:105–132 (1982).
Lai, L.-P., et al., *Gene* 151:339–340 (1994).
Lazzara, R. *Eur Heart J* 14:H88–H92 (1993).
Lehmann, M. H., et al., *J Am Coll Cardiol* 29:93–99 (1997).
Locati, E. H., et al., *Circulation* 97:2237–2244 (1998).
Luo, C. H. & Rudy, Y. A. *Circ Res* 74:1071–1096 (1994).
Makkar, R. R., et al., *JAMA* 270:2590–2597 (1993).
Maniatis et. al. in *Molecular Cloning: A Laboratory Manual*, Cold Spring Harbor, N.Y., p 280–281 (1982).
Mcdonald, T. V., et al., *Nature* 388:289–292 (1997).
Messing et al., *Third Cleveland Symposium on Macro Molecular and Recombinant DNA* Ed. Walton, A., (Elsevier, Amsterdam) (1981).
Mohammad, S., et al., *Am. J. Physiol. Heart Circ. Physiol.* 273:H2534–H2538(1997).
Napolitano, C., et al., *Circulation* 96:1–211(1997).
Nattel, S. *Cardiovasc.Res.* 37:567–577 (1998).
Needleman et al., *J. Mol. Biol.* 48:443 (1970).
Orita, M., et al., *Proc Natl Acad Sci USA* 86:2766–2770 (1989).
*PCR. A Practical Approach*, ILR Press, Eds. McPherson, et al. (1992).
Po, S. S., et al., *J Cardiovasc Pharmacol* 33:181–185 (1999).
Priori, S. G., et al., *Eur Heart J* 18:324(1997).
Rampe, D., et al., *FEBS Lett* 417:28–32 (1997).
Roden, D. M. *PACE* 21:1029–1034 (1998).
Roden, D. M., *Pace-Pacing and Clinical Electrophysiology* 21:1029–1034 (1998).
Roden, D. M., *Am J Cardiol* 72:44B–49B (1993).
Roden, D. M. *Am J Cardiol* 82:49I–57I (1998).
Roden, D. M., et al., *Circulation* 94:1996–2012 (1996).
Roden, D. M., *N. Engl. J. Med.* 331:785–791 (1994).
Saiki et al., *Bio/Technology* 3:1008–1012 (1985).
Sambrook, J., et al., *Molecular Cloning: a Laboratory Manual* (Cold Spring Harbor, New York, N.Y., 1989).
Sanguinetti, M. C., et al., *Nature* 384:80–83 (1996).
Schmidt, R. D., *Clin. Chim. Acta.* 74:39–42 (1977).
Schoft, J. J., et al., 57:1114–1122 (1995).
Schulze-Bahr, E., et al., *Circulation* 96:1–211(1997).
Schwartz et al., eds., *Atlas of Protein Sequence and Structure*, National Biomedical Research Foundation, pp. 357–358 (1979).
Smith et al., *Adv. Appl. Math.* 2:482 (1981).
Splawski, I., et al., *Nature Genet.* 17:338–340 (1997).
Suessbrich, H., et al., *FEBS Lett* 385:77–80 (1996).
Tan, H. L., et al., *Ann. Intem. Med.* 122:701–714 (1995).
Tesson, F., et al., *J Mol Cell Cardiol* 28:2051–2055 (1996).
U.S. Pat. No. 4,683,195
U.S. Pat. No. 5,648,061
U.S. Pat. No. 5,651,964
U.S. Pat. No. 5,741,957
U.S. Pat. No. 5,625,125
U.S. Pat. No. 5,641,484
U.S. Pat. No. 5,643,567
U.S. Pat. No. 5,614,396
U.S. Pat. No. 4,196,265
U.S. Pat. No. 4,458,066
U.S. Pat. No. 4,554,101
U.S. Pat. No. 5,646,008
U.S. Pat. No. 4,683,202
U.S. Pat. No. 4,736,866
U.S. Pat. No. 4,769,331
U.S. Pat. No. 4,965,188
U.S. Pat. No. 5,162,215
U.S. Pat. No. 5,279,833
U.S. Pat. No. 5,286,634
U.S. Pat. No. 5,399,346
U.S. Pat. No. 5,489,742
U.S. Pat. No. 5,550,316
U.S. Pat. No. 5,573,933
Vincent, G. M. *Annu. Rev. Med.* 49:263–274 (1998).
Viswanathan, P. C., et al., *Circulation* 99:2466–2474 (1999).
Wang, Q., et al., *Nature Genet.* 12:17–23 (1996).
Wang, Q., et al., *Cell* 80:805–811 (1995).
Weissenburger, J., et al., *Clin Exp Allergy* 29 (Suppl. 3):190–196 (1999).
Wetmur & Davidson, *J. Mol. Biol.* 31:349–370 (1968).
Woosley, R. L., et al., *JAMA* 269:1532–1536 (1993).
Yang, T., et al., *Circ Res* 77:1246–1253 (1995).
Zeng, J., et al., *Circ Res* 77:140–152 (1995).

It will be understood that various details of the invention can be changed without departing from the scope of the invention. Furthermore, the foregoing description is for the purpose of illustration only, and not for the purpose of limitation—the invention being defined by the claims.

What is claimed is:

1. A method of screening for susceptibility to a drug-induced cardiac arrhythmia in a subject, the method comprising:
   (a) obtaining a biological sample from the subject; and
   (b) detecting a D85N polymorphism of a KCNE1 nucleic acid encoding a cardiac potassium channel minK subunit polypeptide in the biological sample from the subject, the presence of the D85N polymorphism indicating the susceptibility of the subject to a drug-induced cardiac arrhythmia.

2. The method of claim 1, wherein the biological sample comprises a nucleic acid sample.

3. The method of claim 2, wherein the D85N polymorphism of the KCNE1 nucleic acid comprises a G to A transition at nucleotide 281 of a cDNA that corresponds to a KCNE1 gene in the subject.

4. The method of claim 3, wherein the G to A transition at nucleotide 281 of the cDNA that corresponds to the KCNE1 gene further comprises a change in a triplet code from GAC to AAC or GAT to AAT, which encodes a minK polypeptide having an asparagine moiety at amino acid 85.

5. The method of claim 2, wherein the polymorphism is detected by amplifying a target nucleic acid in the nucleic acid sample from the subject using an amplification technique.

6. The method of claim 5, wherein the polymorphism is detected by amplifying a target nucleic acid in the nucleic acid sample from the subject using an oligonucleotide pair, wherein a first oligonucleotide of the pair hybridizes to a first portion of the KCNE1 nucleic acid, wherein the first portion includes the D85N polymorphism of the KCNE1 nucleic acid, and wherein the second of the oligonucleotide pair hybridizes to a second portion of the KCNE1 nucleic acid that is adjacent to the first portion.

7. The method of claim 6, wherein the first portion of the KCNE1 nucleic acid includes nucleotide 281 of a cDNA that corresponds to a KCNE1 gene in the subject.

8. The method of claim 7, wherein the first and the second oligonucleotides each further comprise a detectable label, and wherein the label of the first oligonucleotide is distinguishable from the label of the second oligonucleotide.

9. The method of claim 8, wherein said label of said first oligonucleotide is a radiolabel, and wherein said label of said second oligonucleotide is a biotin label.

10. The method of claim 2, wherein the polymorphism is detected by sequencing a target nucleic acid in the nucleic acid sample from the subject.

11. The method of claim 10, wherein the sequencing comprises dideoxy sequencing.

12. The method of claim 2, wherein the detecting comprises determining an AAC or AAT nucleotide sequence in the codon encoding amino acid 85 of a KCNE1 polypeptide as indicative of a D to N substitution.

13. The method of claim 12, wherein the detecting a polymorphism further comprises contacting the nucleic acid sample with a KCNE1 allele specific oligonucleotide.

14. The method of claim 13, wherein the allele specific oligonucleotide has a sequence as set forth in SEQ ID NO:9.

15. The method of claim 1 or 2, wherein the subject is a human subject.

16. The method of claim 13, wherein the detecting a polymorphism further comprises:
   (a) hybridizing the KCNE1 allele specific oligonucleotide with the nucleic acid sample under stringent hybridization conditions; and
   (b) detecting a heteroduplex comprising the KCNE1 allele specific oligonucleotide and a nucleic acid molecule of the biological sample, whereby the polymorphism is detected.

* * * * *

SEQUENCE LISTING

<160> NUMBER OF SEQ ID NOS: 11

<210> SEQ ID NO 1
<211> LENGTH: 436
<212> TYPE: DNA
<213> ORGANISM: Homo sapiens
<220> FEATURE:
<221> NAME/KEY: CDS
<222> LOCATION: (29)..(418)
<300> PUBLICATION INFORMATION:
<303> JOURNAL: Biochem. Biophys. Res. Commun.
<304> VOLUME: 161
<306> PAGES: 176-181
<307> DATE: May-1989
<308> DATABASE ACCESSION NUMBER: GenBank M26685
<309> DATABASE ENTRY DATE: 1994-03-30

<400> SEQUENCE: 1

```
ctgcagcagt ggaaccttaa tgcccagg atg atc ctg tct aac acc aca gcg        52
                                Met Ile Leu Ser Asn Thr Thr Ala
                                  1               5 gtg acg ccc ttt ctg acc aag ctg tgg cag gag aca gtt cag cag ggt      100
Val Thr Pro Phe Leu Thr Lys Leu Trp Gln Glu Thr Val Gln Gln Gly
         10                  15                  20 ggc aac atg tcg ggc ctg gcc cgc agg tcc ccc cgc agc agt gac ggc      148
Gly Asn Met Ser Gly Leu Ala Arg Arg Ser Pro Arg Ser Ser Asp Gly
 25                  30                  35                  40 aag ctg gag gcc ctc tac gtc ctc atg gta ctg gga ttc ttc ggc ttc      196
Lys Leu Glu Ala Leu Tyr Val Leu Met Val Leu Gly Phe Phe Gly Phe
                 45                  50                  55 ttc acc ctg ggc atc atg ctg agc tac atc cgc tcc aag aag ctg gag      244
Phe Thr Leu Gly Ile Met Leu Ser Tyr Ile Arg Ser Lys Lys Leu Glu
             60                  65                  70 cac tcg aac gac cca ttc aac gtc tac atc gag tcc gat gcc tgg caa      292
His Ser Asn Asp Pro Phe Asn Val Tyr Ile Glu Ser Asp Ala Trp Gln
         75                  80                  85 gag aag gac aag gcc tat gtc cag gcc cgg gtc ctg gag agc tac agg      340
Glu Lys Asp Lys Ala Tyr Val Gln Ala Arg Val Leu Glu Ser Tyr Arg
     90                  95                 100 tcg tgc tat gtc gtt gaa aac cat ctg gcc ata gaa caa ccc aac aca      388
Ser Cys Tyr Val Val Glu Asn His Leu Ala Ile Glu Gln Pro Asn Thr
105                 110                 115                 120 cac ctt cct gag acg aag cct tcc cca tga accccaccac tggctaaa          436
His Leu Pro Glu Thr Lys Pro Ser Pro
                125
```

<210> SEQ ID NO 2
<211> LENGTH: 129
<212> TYPE: PRT
<213> ORGANISM: Homo sapiens

<400> SEQUENCE: 2

```
Met Ile Leu Ser Asn Thr Thr Ala Val Thr Pro Phe Leu Thr Lys Leu
  1               5                  10                  15

Trp Gln Glu Thr Val Gln Gln Gly Gly Asn Met Ser Gly Leu Ala Arg
             20                  25                  30

Arg Ser Pro Arg Ser Ser Asp Gly Lys Leu Glu Ala Leu Tyr Val Leu
         35                  40                  45

Met Val Leu Gly Phe Phe Gly Phe Phe Thr Leu Gly Ile Met Leu Ser
     50                  55                  60

Tyr Ile Arg Ser Lys Lys Leu Glu His Ser Asn Asp Pro Phe Asn Val
```

```
                65                  70                  75                  80
Tyr Ile Glu Ser Asp Ala Trp Gln Glu Lys Asp Lys Ala Tyr Val Gln
                        85                  90                  95

Ala Arg Val Leu Glu Ser Tyr Arg Ser Cys Tyr Val Val Glu Asn His
            100                 105                 110

Leu Ala Ile Glu Gln Pro Asn Thr His Leu Pro Glu Thr Lys Pro Ser
        115                 120                 125

Pro

<210> SEQ ID NO 3
<211> LENGTH: 436
<212> TYPE: DNA
<213> ORGANISM: Homo sapiens
<220> FEATURE:
<221> NAME/KEY: CDS
<222> LOCATION: (29)..(418)

<400> SEQUENCE: 3
ctgcagcagt ggaaccttaa tgcccagg atg atc ctg tct aac acc aca gcg         52
                                Met Ile Leu Ser Asn Thr Thr Ala
                                  1               5 gtg acg ccc ttt ctg acc aag ctg tgg cag gag aca gtt cag cag ggt       100
Val Thr Pro Phe Leu Thr Lys Leu Trp Gln Glu Thr Val Gln Gln Gly
     10                  15                  20 ggc aac atg tcg ggc ctg gcc cgc agg tcc ccc cgc agc agt gac ggc       148
Gly Asn Met Ser Gly Leu Ala Arg Arg Ser Pro Arg Ser Ser Asp Gly
 25                  30                  35                  40 aag ctg gag gcc ctc tac gtc ctc atg gta ctg gga ttc ttc ggc ttc       196
Lys Leu Glu Ala Leu Tyr Val Leu Met Val Leu Gly Phe Phe Gly Phe
                 45                  50                  55 ttc acc ctg ggc atc atg ctg agc tac atc cgc tcc aag aag ctg gag       244
Phe Thr Leu Gly Ile Met Leu Ser Tyr Ile Arg Ser Lys Lys Leu Glu
             60                  65                  70 cac tcg aac gac cca ttc aac gtc tac atc gag tcc aat gcc tgg caa       292
His Ser Asn Asp Pro Phe Asn Val Tyr Ile Glu Ser Asn Ala Trp Gln
         75                  80                  85 gag aag gac aag gcc tat gtc cag gcc cgg gtc ctg gag agc tac agg       340
Glu Lys Asp Lys Ala Tyr Val Gln Ala Arg Val Leu Glu Ser Tyr Arg
     90                  95                 100 tcg tgc tat gtc gtt gaa aac cat ctg gcc ata gaa caa ccc aac aca       388
Ser Cys Tyr Val Val Glu Asn His Leu Ala Ile Glu Gln Pro Asn Thr
105                 110                 115                 120 cac ctt cct gag acg aag cct tcc cca tga accccaccac tggctaaa          436
His Leu Pro Glu Thr Lys Pro Ser Pro
                125

<210> SEQ ID NO 4
<211> LENGTH: 129
<212> TYPE: PRT
<213> ORGANISM: Homo sapiens

<400> SEQUENCE: 4

Met Ile Leu Ser Asn Thr Thr Ala Val Thr Pro Phe Leu Thr Lys Leu
  1               5                  10                  15

Trp Gln Glu Thr Val Gln Gln Gly Gly Asn Met Ser Gly Leu Ala Arg
             20                  25                  30

Arg Ser Pro Arg Ser Ser Asp Gly Lys Leu Glu Ala Leu Tyr Val Leu
         35                  40                  45

Met Val Leu Gly Phe Phe Gly Phe Phe Thr Leu Gly Ile Met Leu Ser
     50                  55                  60
```

```
Tyr Ile Arg Ser Lys Lys Leu Glu His Ser Asn Asp Pro Phe Asn Val
 65                  70                  75                  80

Tyr Ile Glu Ser Asn Ala Trp Gln Glu Lys Asp Lys Ala Tyr Val Gln
                 85                  90                  95

Ala Arg Val Leu Glu Ser Tyr Arg Ser Cys Tyr Val Val Glu Asn His
            100                 105                 110

Leu Ala Ile Glu Gln Pro Asn Thr His Leu Pro Glu Thr Lys Pro Ser
        115                 120                 125

Pro

<210> SEQ ID NO 5
<211> LENGTH: 20
<212> TYPE: DNA
<213> ORGANISM: Homo sapiens

<400> SEQUENCE: 5
tgcagcagtg gaaccttaat                                              20

<210> SEQ ID NO 6
<211> LENGTH: 20
<212> TYPE: DNA
<213> ORGANISM: Homo sapiens

<400> SEQUENCE: 6
cttcttggag cggatgtagc                                              20

<210> SEQ ID NO 7
<211> LENGTH: 20
<212> TYPE: DNA
<213> ORGANISM: Homo sapiens

<400> SEQUENCE: 7
actgggattc ttcggcttct                                              20

<210> SEQ ID NO 8
<211> LENGTH: 20
<212> TYPE: DNA
<213> ORGANISM: Homo sapiens

<400> SEQUENCE: 8
tttagccagt ggtgggttc                                               20

<210> SEQ ID NO 9
<211> LENGTH: 18
<212> TYPE: DNA
<213> ORGANISM: Homo sapiens

<400> SEQUENCE: 9
gagtccaatg cctggcaa                                                18

<210> SEQ ID NO 10
<211> LENGTH: 84
<212> TYPE: DNA
<213> ORGANISM: Homo sapiens

<400> SEQUENCE: 10
tacatccgct ccaagaagct ggagcactcg aacgacccat tcaacgtcta catcgagtcc  60
aatgcatggc aagagaagga caag                                        84

<210> SEQ ID NO 11
```

-continued

```
<211> LENGTH: 30
<212> TYPE: DNA
<213> ORGANISM: Homo sapiens

<400> SEQUENCE: 11
tcgatcgtct agagatcagc ggccgctctt                                        30
```